United States Patent [19]

Kuna et al.

[11] Patent Number: 5,436,222
[45] Date of Patent: Jul. 25, 1995

[54] USE OF PLATELET FACTOR 4 TO TREAT INFLAMMATORY DISEASES

[75] Inventors: Piotr Kuna, Port Jefferson; Allen P. Kaplan, St. James, both of N.Y.

[73] Assignee: The Research Foundation of State University of New York, Albany, N.Y.

[21] Appl. No.: 31,773

[22] Filed: Mar. 15, 1993

[51] Int. Cl.⁶ .................... A61K 38/00; A61K 38/02; C07K 5/00; C07K 7/00
[52] U.S. Cl. .................... 514/12; 530/300; 530/324; 514/826; 514/886
[58] Field of Search .............. 514/12, 826, 886; 530/300, 324; 435/69.1

[56] References Cited

FOREIGN PATENT DOCUMENTS

WO92/01465  2/1992  WIPO .............. A61K 37/02

OTHER PUBLICATIONS

Brindley et al, *J. Clin. Invest*, vol. 72, pp. 1218–1223, (1983).
Averill et al., *Am. Rev. Respir. Dis.*, vol. 145, No. 2, Feb. 1992, pp. 571–576.
Knauer et al., *Int. Archs Allergy appl. Immun.* vol. 74, pp. 29–35, 1984.
Alam et al., *J. Clin. Invest.*, 89:723 (1992).
Alam et al., *J. Clin. Invest., 82:2056 (1988).*
Bischoff et al., *Biochem. Biophys. Res. Commun.*, 179:628–33 (1991).
Fisher et al., *J. Allergy Clin. Immunol.,* 91(1):Abstracts 225, No. 339 (1992).
Fisher et al., *J. Allergy Clin. Immunol.,* 89(1):Abstracts 165, No. 81 (1992).
Goetzl et al., *J. Exp. Med.,* 158:731–737 (1983).
Hirai et al., *J. Immunol.,* 141:3958 (1988).
Hirai et al., *J. Exp. Med.,* 172:1525 (1990).
Irvin, *J. Allergy Clin. Immunol.,* 90(3):521–533 (1992).
Knauer et al., *N. Engl. J. Med.,* 304:1404 (1981).
Koch et al., *J. Clin. Invest.,* 90:772 (1992).
Kuna et al., *J. Allergy Clin. Immunol.,* 91: Abstracts 314, No. 695 (1993).
Kuna et al., *J. Immunol.,* 149:636 (1992).
Kuna et al., *J. Immunol.* 147:1920–1924 (1991).
Kuna et al., *J. Immunol.* 150:1932–1943 (Mar., 1993).
Kuna et al., *J. Exp. Med.,* 175:489 (1992).
Maione et al., *Science,* 247:77–79 (1990).
McFadden, et al., Chap. 257 "Asthma," *Harrison's Principles of Internal Medicine,* 1349–1354 (McGraw-Hill, Inc. 1977).
Metzger et al., *J. Allergy Clin. Immunol.,* 91(1):Abstracts 163, No. 89 (1983).
Metzger et al., Chapter 35, "Late Phase Asthma in an Allergic Rabbit Model", pp. 347–362.
Osterman et al., *Biochem. and Biophys. Res. Comm.,* 107(1):130–135 (1982).
Wasserman et al., *J. Allerg Clin. Immunol.,* 74:275–279 (1984).

*Primary Examiner*—Jill Warden
*Assistant Examiner*—A. M. Davenport
*Attorney, Agent, or Firm*—Fish & Richardson

[57] ABSTRACT

A method of treating an inflammatory disease in a mammal, e.g., a human, by inhibiting pro-inflammatory mediator release from basophils or mast cells in the human, by administering to the human a therapeutically effective amount of purified or recombinant platelet factor 4 (PF4), a PF4 analog, or a peptide fragment of PF4 or the analog.

15 Claims, 3 Drawing Sheets

USE OF PLATELET FACTOR 4 TO TREAT INFLAMMATORY DISEASES

STATEMENT AS TO FEDERALLY SPONSORED RESEARCH

This invention was made with Government support under Grant No. 1526N awarded by the National Institutes of Health. The Government may have certain rights in the invention.

BACKGROUND OF THE INVENTION

This invention relates to the use of a specific protein to treat inflammatory diseases.

Inflammatory diseases are caused by the secretion of numerous pro-inflammatory mediators, such as histamine, from so-called "primary allergic" cells, i.e., basophils and mast cells. Inflammatory, e.g., allergic, diseases, include a wide range of disorders such as allergic rhinitis, urticaria, allergic conjunctivitis, atopic dermatitis, and allergic contact dermatitis. One of the most prevalent allergic diseases is asthma. It is estimated that 5% of the population of industrialized countries suffer from asthma. In the United States, reported cases of asthma have risen from 3% in 1979 to 4% in 1987, with over 10 million people currently affected.

Asthma is defined as an inflammation of the airways associated with bronchial hyper-responsiveness and bronchoconstriction, causing intermittent wheezing and coughing. Asthma is associated with airway inflammation, increased mucous secretion, mucosal edema, smooth muscle contraction, mast cell degranulation, and bronchial hyper-responsiveness. It is currently believed that asthma and other allergic diseases are caused by hypersensitivity reactions induced by primary allergic cells, i.e., basophils and mast cells, which are highly specialized effector cells of the immune system. Both cells store and synthesize large quantities of various mediators of inflammation and express high affinity IgE receptors. These pro-inflammatory mediators include, e.g., histamine, tryptase (from mast cells), leukotrienes ($C_4$, $D_4$, $E_4$), Platelet Activating Factor (PAF), a variety of cytokines, and other neutral proteases.

Basophils and their mediators are involved, for example, in "cutaneous basophil hypersensitivity," and in the so-called "late phase allergic reaction" in the upper airways and skin; however, the mechanism responsible for protracted histamine release seen during this late phase allergic reaction remains obscure. The late phase appears 4 to 6 hours after an allergen-dependent immediate hypersensitivity reaction, and it seems that factors other than allergen or IgE antibody are responsible for basophil and/or mast cell secretion during that time.

In 1979, Thueson et al. reported that the crude supernatant of mononuclear cell cultures contain a factor (Histamine Releasing Factor or HRF) which stimulates basophils and/or mast cells to release histamine. *J. Immunol.*, 122:623 (1979). Dvorak et al. later described that HRF is also chemotactic for basophils. *Clin. Immunol. Immunopathol.*, 32:142 (1984). A major constituent of HRF activity is so-called Monocyte Chemotactic and Activating Factor/Monocyte Chemoattractant Protein-1 (MCAF/MCP-1), which is the most potent chemokine to release histamine from basophils. See, e.g., Kuna et al., *J. Exp. Med.*, 175:489 (1992) and Alam et al., *J. Clin. Invest.*, 89:723 (1992).

HRFs such as MCAF/MCP-1 are thought to contribute significantly to the protracted histamine release and basophil and/or mast cell degranulation seen in a wide variety of immunologic disorders including chronic urticaria, atopic dermatitis, asthma, and rheumatoid arthritis, although the specific contribution of MCAF/MCP-1 to histamine release in such disorders has not yet been determined. However, MCAF/MCP-1 has been recently reported to be elevated in the synovial fluid of patients with rheumatoid arthritis. Koch et al., *J. Clin. Invest.*, 90:772 (1992). The mean concentration found was $25.5 \pm 8.1$ ng/ml which corresponds to $3 \times 10^{-9}$ M, at which concentration it is both a chemotactic factor and activates of basophils to release histamine.

In addition, Platelet Factor 4 (PF4) has been shown to induce basophils to release histamine. Brindley et al., *J. Clin. Invest.* 72:1218–23 (1983). The baseline concentration of PF4 in the sera of both asthmatics and non-asthmatics donors is $4.6 \pm 0.3$ ng/ml ($5.9 \times 10^{-10}$ M), but when asthmatics are challenged with allergen, the PF4 level rises to $7.9 \pm 1.82$ ng/m. Knauer et al., *N. Engl. J. Med.* 304:1404 (1981).

The treatment of respiratory allergic diseases such as asthma has undergone fundamental changes over the last decade. Emphasis has shifted from making the patient as comfortable as possible by eliminating bronchoconstricting symptoms to treating the underlying condition of the inflammatory response of the airways so as to prevent long-term bronchial destruction. The two primary goals in the management of asthma are to limit bronchial hyper-responsiveness and reduce inflammation of the airways.

First line anti-inflammatory therapy for asthma is the use of inhaled steroids, which are often used concomitantly with inhaled $\beta$-agonist-type bronchodilators. Beta-agonists used in this fashion provide prompt relief with few side effects. However, a growing number of studies suggests that one of these $\beta$-agonists, fenoterol, may be responsible for an increasing number of deaths of asthmatic patients. Beta-agonists are also contraindicated in patients with coronary disease, as these drugs increase the heart rate. Inhaled cromolyn sodium can be added to such regimens when further therapy is needed. Antihistamines are commonly used to treat allergic rhinitis and urticaria, but often lack complete efficacy and are ineffective against asthma.

Adjunctive therapy includes the use of oral or intravenous theophylline, a bronchodilator used to prevent broncho-constriction, and/or oral $\beta$-agonists. These have narrow therapeutic spectrums and side effects are common. Oral corticosteroids are used in refractory patients; however, low doses are not always effective, and high doses have serious adverse effects due to their toxicity. For example, high blood levels of corticosteroids are associated with Cushing's Syndrome, osteoporosis, and cataracts. As a result, none of the currently available treatment regimens are effective in curing asthma, or in substantially avoiding adverse side effects.

SUMMARY OF THE INVENTION

Applicants have discovered that PF4 inhibits pro-inflammatory mediator release from primary allergic cells, e.g., basophils and mast cells, in a time and dose dependent fashion. These mediators include preformed mediators such as histamine, cytokines, and tryptase (in mast cells), and synthesized mediators such as leukotrienes, prostaglandins, and PAF.

Based on this discovery, applicants have developed a method of treating an inflammatory disease in a mammal, e.g., a human, e.g., by inhibiting pro-inflammatory mediator release from basophils or mast cells in the mammal, by administering to the mammal a therapeutically effective amount of purified or recombinant platelet factor 4 (PF4), a PF4 analog, or peptide fragment of PF4 or the analog. This method substantially avoids adverse side effects and any immunological reaction to the therapy.

As used herein, the term "inflammatory disease" refers to any disease characterized by an increased secretion of pro-inflammatory mediators, compared to a basal level, by primary allergic cells, i.e., basophils and mast cells. The term "inflammatory diseases" includes rheumatoid arthritis, scleroderma, and the allergic diseases, which are inflammatory diseases caused by a specific allergen.

Allergic diseases include respiratory allergic diseases such as asthma and allergic rhinitis ("hay fever"), and various types of urticaria, e.g., cold-induced urticaria, angioedema, allergic conjunctivitis, atopic dermatitis, allergic contact dermatitis, drug allergies, e.g., to penicillin or sulfa drugs, insect sting allergies, and systemic anaphylaxis.

A "therapeutically effective amount" of a protein is a dosage that improves the symptoms of the inflammatory, e.g., allergic, disease by inhibiting the secretion of pro-inflammatory mediators, e.g., histamine, from the primary allergic cells.

In this method, the PF4, PF4 analog, or peptide fragment may be mixed with a pharmaceutically acceptable carrier, and can be administered systemically at a dosage of between 1 to 10 mg/m$^2$ of body surface area, or 0.5 to 500 µg/kg, preferably 20 to 200 µg/kg, of the body weight, of the mammal. The PF4, PF4 analog, or fragment also can be administered by inhalation at a dosage of between 10 ng to 1 mg, and preferably 100 ng to 100 µg, per inhalation. For topical administration, the dosage is 100 ng to 10 mg/surface area/day.

The PF4, PF4 analog, or fragment can be administered by intravenous, intraarterial, intramuscular, subcutaneous, oral, or other systemic administration, or by transdermal, intranasal, or other topical administration. The PF4, PF4 analog, or fragment can also be administered to the mammal together with a different histamine-release inhibiting agent, such as another protein, analog, or peptide fragment.

The invention also features a method of inhibiting allergic disease, e.g., a respiratory allergic disease, in a mammal, e.g., a human, by administering to the mammal a therapeutically effective amount of a purified or recombinant platelet factor 4 (PF4), or a PF4 analog or peptide fragment of PF4 or the analog.

The respiratory allergic disease treated according to this method may be asthma, and the PF4, PF4 analog, or fragment can be administered by inhalation at a dosage of between 10 ng to 1 mg, and preferably 100 ng to 100 µg, per inhalation.

In addition, the invention features a method of treating an inflammatory disease in a mammal, e.g., a human, e.g., by inhibiting pro-inflammatory mediator release from basophils or mast cells in the mammal, by administering to the mammal a therapeutically effective amount of a synthetic or recombinant protein having the biological activity of purified or recombinant PF4, wherein the protein has the same amino acid sequence of PF4 with the exception of conservative amino acid substitutions.

Other features and advantages of the invention will be apparent from the detailed description, and from the claims.

DETAILED DESCRIPTION

Applicants have discovered that PF4 inhibits or decreases the release of pro-inflammatory mediators, e.g., histamine and cytokines, from primary allergic cells, e.g., basophils and mast cells, in a time and dose dependent fashion. More importantly, based on these results, applicants have discovered that this inhibition can be used to treat inflammatory diseases such as allergic diseases like asthma in humans and other animals.

PLATELET FACTOR 4

Purified Human PF4

PF4 is a 70-residue secreted platelet protein with a molecular weight of approximately 7.8 Kd which is released during platelet aggregation. Native human PF4 can be purified from human platelets by known techniques, for example as described in Handin, et al., *J. Biol. Chem.*, 251:4273–4282 (1976), which is incorporated herein by reference. Purified human PF4 also can be purchased from J. R. Scientific Inc., Woodland, Calif.

In addition, PF4 is a well-known protein which has been completely sequenced, see, e.g., Deuel, et al., *P.N.A.S. USA*, 78:4585–4587 (1981), Poncz et al., *Blood*, 69:219 (1987), which are incorporated herein by reference, and can be produced by recombinant means as described, e.g., in Myers et al., *Protein Ex. Purif.*, 2:136–143 (1991), Cooke et al., *Circulation*, 85:1102–1109 (1992), also incorporated herein by reference, or as described below.

Production of Recombinant PF4

Recombinant PF4 can be produced in *E. coli* as an N-terminal fusion protein containing a unique methionine residue immediately preceding the PF4 portion. More specifically, an expression plasmid pPF4-211 has been constructed by cloning a synthetic gene encoding native sequence PF4 into the multiple restriction site region of plasmid pREV2.2 (deposited by Repligen Corporation on Jul. 30, 1986 under accession number NRRL B-18091). Codon usage in the synthetic gene was optimized for expression in *E. coli*, and synthetic DNA linkers were included on each end of the gene to facilitate the directional insertion of the PF4 gene into the vector. The restriction sites HindIII and SmaI were chosen for insertion into pREV2.2. The resulting construct, pPF4-211, expressed a fusion protein containing 34 amino acids of *E. coli* β-glucuronidase (BG) separated from the PF4 sequence by a unique methionine residue.

Cells expressing the fusion protein were subjected to lysozyme (1 mg/g cells), DNase I (500 units/100 g cells) and bead mill treatments. The lysis pellet containing the fusion protein was treated with CNBr (10 g/100 g cells) in 70% formic acid to cleave the fusion protein at the methionine between the BG and PF4 portions. Following evaporation of the CNBr/formic acid, the recombinant protein was extracted with 200 ml of 50 mM Tris-Cl, pH 7.6, 5 mM EDTA, and 10 mM DTT per 100 g of cell starting material. Native sequence rPF4-211 was purified by binding the protein to heparin agarose, removing contaminating proteins with 0.6 M NaCl, and eluting with 1.2 M NaCl. The resulting material was dialyzed into 20 mM sodium acetate, pH 4.0, and analyzed on a 15% SDS-PA gel stained with Coomassie Brilliant Blue. Minor contaminants could be removed using $C_4$ reverse phase high pressure liquid chromatography (HPLC) to prepare the protein for in vivo use.

Production of PF4 Analogs that Inhibit Mediator Release

It is known that proteins of identified structure and function can be constructed by changing the amino acid sequence if such changes do not significantly alter the protein secondary structure. Kaiser et al., *Science*, 223:249–255 (1984). Accordingly, the subject invention includes analogs (mutants) of the sequence of the naturally occurring PF4 which exhibit substantially the same, higher, or lower histamine-release inhibiting activity of PF4.

Synthetic genes encoding mutant PF4 analogs that have the ability to inhibit pro-inflammatory mediator release from primary allergic cells, e.g., basophils, can be constructed by changing the codons for specific residues in the sequence of naturally occurring PF4, e.g., near the C-terminus of PF4, to sequences encoding different amino acids, e.g., by cassette mutagenesis. Such analogs include a portion of the sequence of PF4, and must have the ability to inhibit the release of histamine by basophils. Such PF4 analogs can be tested for efficacy for the methods of the invention in the in vitro histamine assay described below, or in the in vivo rabbit asthma model, also described below.

Analogs according to the invention may include conservative amino acid substitutions, as long as the analog has a histamine-release inhibiting activity. As used herein, the term conservative amino acid substitution means the substitution of an amino acid with another amino acid that is of the same class. Amino acids may be placed in the following classes: basic, hydrophobic, acidic, polar, and amide. Substitutions in which an amino acid of one class is replaced with another amino acid of the same class fall within the scope of the subject invention so long as the substitution does not materially alter the biological activity of the compound. The table below provides a listing of examples of amino acids belonging to each class.

| Class of Amino Acid | Example of Amino Acids |
| --- | --- |
| Basic | K, R, H |
| Hydrophobic | A, L, I, V, P, F, W, Y, M |
| Acidic | E, D |
| Polar | S, T, N, Q, C |
| Amide | Q, N |

To use a synthetic gene encoding a mutant PF4 analog, linkers can be included on each end of the synthetic gene to facilitate the directional insertion into a vector such as pREV2.2 as described above. The mutant proteins can be expressed, cleaved, and extracted as described above. The extracts are then purified using ion-exchange chromatography, and eluted with a gradient of 0–1 M NaCl. PF4 analog proteins generally elute at approximately 0.5 M NaCl and are dialyzed into 20 mM acetate buffer, pH 5. The samples are further purified by reverse phase HPLC.

The PF4 analogs of the invention can also be synthesized by standard techniques as described below with respect to peptide fragments.

PF4 Peptide

Peptide fragments of PF4, or PF4 analogs, can also be used in the methods of the present invention. As used herein, a peptide fragment of PF4 is some portion of the full length native or recombinant PF4, or mutant PF4 analog, that has substantially the same, lower, or preferably higher, ability as native PF4 to inhibit histamine release from basophils. Various peptide fragments of PF4 have been purified and studied. PF4 peptide fragments C-12, C-13, and C-41 and their biological activities are described in Maione et al., *Science*, 247:77–79 (1990), which is incorporated herein by reference. These peptide fragments have various characteristics of full length PF4. For example, the C-13 peptide of PF4 is chemotactic for neutrophils and monocytes, Osterman et al., *Biochem. and Biophys. Res. Comm.*, 107(1):130–135 (1982). Accordingly, these peptide fragments may be useful in the methods of the present invention.

These peptide fragments can be prepared by standard solid phase synthesis procedures, e.g., using an Applied Biosystems Inc. 430 automated synthesizer according to standard methods using Boc/benzyl protected amino acids and anhydrous hydrogen fluoride cleavage/deprotection. See, e.g., Stewart et al., *Solid Phase Peptide Synthesis*, Pierce Chemical Com. Rockford, Ill., 1984.

The peptides are then cleaved from the solid support and deblocked, and purified to greater than 98% homogeneity by one pass over a 2×25 cm reverse phase HPLC column (Vydac) using a water/acetonitrile (0.1% trifluoroacetic acid) gradient. Peptide fragments can be identified and quantitated using a Waters Picotag (Milford, Mass.) amino acid analysis system and Electrospray Mass spectrometry according to standard methods.

Synthetic peptide fragments corresponding to sequences of PF4 as small as 13 amino acids in length may be useful for the methods of the invention, as long as they maintain the ability to inhibit histamine release from basophils. The use of short peptides, such as the C-13 peptide, offer several advantages over whole recombinant PF4 such as reduced dosage (weight basis), reduced likelihood of antigenicity, and greater likelihood of effectiveness in novel dosage forms. Additionally, since small peptides are generally less antigenic than larger proteins, short PF4 peptides can be used advantageously for oral and transdermal administration.

Using the methods of this application, a researcher could prepare and readily test analogs and peptide fragments which could be expected to have the desired properties. In addition, fragments of the PF4 mutant analogs described above can also be made and tested.

Other Proteins

Recombinant human MCAF/MCP-1 (rh-MCAF/MCP-1), with a maximal chemotactic activity on human monocytes at 20 ng/ml, can be purchased from Pepro Tech Inc., Rocky Hill, N.J. Recombinant MCAF/MCP-1 can also be produced by standard recombinant techniques based on the amino acid sequence published in, e.g., Oppenheim, et al., *Annu. Rev. J. Immunol.*, 9:617-648 (1991), which is incorporated herein by reference.

Cell Preparation

The procedure for leukocyte isolation has been described previously, Kaplan et al., *J. Immunol.*, 135:2027 (1985), which is incorporated herein by reference. Briefly, the cells were prepared by dextran sedimentation (0.6% dextran, 0.6% glucose, 0.02 M EDTA), the basophil containing layer was washed twice with HEPES-buffered saline containing 0.3% HSA (HBS-HSA), and the cells were resuspended in HBS-HSA containing 2 mM $CaCL_2$ and 2 mM $MgCl_2$. In some experiments basophils were purified from peripheral blood on a discontinuous Percoll gradient according to the method described by Leonard at al., *J. Leuk. Biol.*, 35:169 (1984), followed by negative selection using magnetic beads coated with goat anti-mouse IgG (Advanced Magnetic Inc., Cambridge, Mass.). The basophils purified by Percoll gradient were incubated in D-PBS, pH 7.4 containing 1% BSA (D-PBS-BSA) plus a mixture of mAb directed against T lymphocytes, B lymphocytes and monocytes (anti-Leu-5b (CD2), anti-Leu-16 (CD20), and anti-Leu-M3 (CD14)(Becton Dickinson, San Jose) for 45 min. at 4° C. The cells were then washed three times in ice-cold D-PBS-BSA, resuspended in 1.0 ml medium, and incubated in a head over head rotor with goat anti-mouse IgG coated magnetic beads (ratio beads:cells 50:1) for 30 min. at 4° C. The immunomagnetic rosetted cells were removed from suspension by a magnetic field. Rosetted cells were collected and resuspended gently into the incubation medium. The magnetic separation was repeated to remove the immunomagnetic rosetted cells from remaining basophils to increase their recovery. The two basophil-containing supernatants were combined, the cells washed twice, and the entire procedure was repeated once again. The purity of the final basophil suspension was determined by staining with alcian blue and was 80%.

Assay of Histamine Release from Basophils

One hundred $\mu l$ of cells, resuspended in HBS-HSA with 2 mM $CaCl_2$ and 2 mM $MgCl_2$ and prewarmed to 37° C. were added to 20 $\mu l$ of tested protein. For inhibitory experiments, the cells were preincubated with PF4 or buffer for 10 min. (except for kinetic experiments) at 37° C. followed by addition of 20 $\mu l$ MCAF/MCP-1, anti-IgE (affinity purified goat anti human IgE antibody (Kirkegaard & Perry Laboratories Inc., Gaithersburg, Md.), or buffer. After incubation the supernatants were separated by centrifugation at 700×g for 5 min at 4° C. and histamine release determined. Two replicate aliquots of cells were boiled to determine total basophil histamine content. All histamine release experiments were performed in duplicate and the results expressed as a percentage of total histamine content. Spontaneous histamine release from the cells was less than 5% and was subtracted from the calculated histamine release.

A radioenzyme assay for histamine was performed in duplicate for each sample by using a modification of the method of Beaven et al., *Clin. Chem. Acta.*, 37:91 (1972), as described previously in Kuna et al., *J. Immunol.*, 149:636 (1992), which are both incorporated herein by reference. Although only histamine was assayed, this released histamine also indicates that other preformed (granule), and subsequently synthesized, pro-inflammatory mediators are being released by the basophils. The latter may require priming the basophils by Interleukin-3, which is likely to occur in vivo in allergic patients.

Statistical Analysis

Results were expressed as mean±SEM. Statistical analysis was performed with Wilcoxon's Signed Rank Test or Student's t-Test paired (as indicated in the text) using the computer program StatWorks (Cricket Software, Philadelphia, Pa.).

PF4-Dependent Histamine Release

Figure 1:
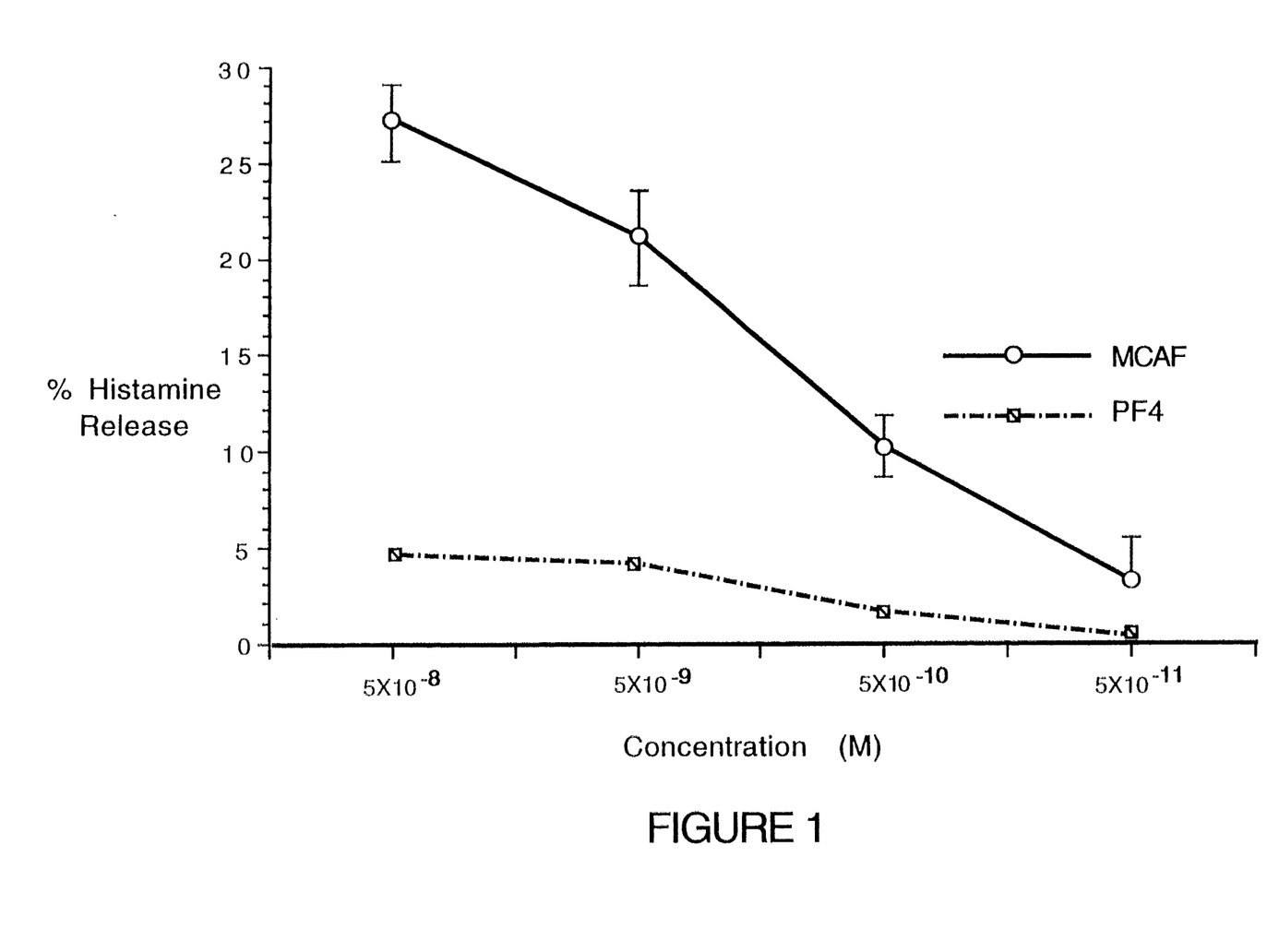
FIG. 1 is a graph showing dose dependent histamine release by MCAF/MCP-1 and PF4.

The ability of PF4 to stimulate histamine release was assessed as indicated in FIG. 1. Human basophils were incubated with PF4 or MCAF/MCP-1 at concentrations ranging from $5 \times 10^{-8}$ to $5 \times 10^{-11}$ M and the percentage of histamine release determined. Each point represents the mean±SEM of six experiments performed in different donors. MCAF/MCP-1 is clearly positive. Thus, MCAF/MCP-1 released more than 10% histamine starting at $5 \times 10^{-10}$ M, while PF4 was clearly negative at the concentrations studied.

Dose-dependent Histamine-release Inhibition by PF4

The effect of preincubation of basophils with PF4 ($5 \times 10^{-8}$ to $5 \times 10^{-11}$ M) upon MCAF/MCP-1 induced histamine release was assessed. PF4 inhibited MCAF/MCP-1-induced histamine release in a dose dependent fashion. A low concentration of MCAF/MCP-1 completely desensitized (taken as 100%) basophils to a subsequent high concentration of MCAF/MCP-1 at an optimal dose range $5 \times 10^{-8}$ to $5 \times 10^{-10}$, which is 2 to 200 fold lower than the optimal MCAF/MCP-1 dose required for histamine release. However, at these concentrations MCAF/MCP-1 itself releases significant (more than 10%) percentage of histamine (FIG. 1). At $5 \times 10^{-11}$ M, MCAF/MCP-1 decreased histamine release by 61.5±2.7%, yet induced less than 5% release.

At a concentration of $5 \times 10^{-9}$ M, PF4 inhibited histamine release by 56.5±2.9%, whereas at this same concentration PF4 released only 4.2±1.1% histamine. PF4 was more effective at the highest concentration studied ($5 \times 10^{-8}$ M), inhibiting histamine release by 72.5±2.1%, and did not release a significant amount of histamine (<5%). At concentrations of $5 \times 10^{-10}$ M and $5 \times 10^{-11}$ M, PF4 decreased histamine release by 42.2±2.6% and 31.6±2.4%, respectively, and induced less than 2% release.

Kinetics of Histamine-release Inhibition by PF4

Kinetics studies of inhibition by PF4 v. MCAF/MCP-1 showed that PF4 inhibition reaches a peak at about ten minutes after challenge with MCAF/MCP-1 ($5 \times 10^{-7}$ M). Leukocytes were preincubated at 37° C. with MCAF/MCP-1 ($5 \times 10^{-10}$ M) or PF4 ($5 \times 10^{-9}$ M) for 0 sec., 15 sec., 30 sec., 1 min., 3 min., 5 min., 10 min., and 30 min., and then MCAF/MCP-1 ($5 \times 10^{-7}$ M) was added for 40 minutes. At time 0, MCAF/MCP-1 induced 35.7±4.2% histamine release, and PF4 induced 36.8±6.6% histamine release. At 3 min., MCAF/MCP-1 and PF4 induced 4.6±2.4% and 26±3.6% histamine release, respectively. At 5 min., MCAF/MCP-1 and PF4 induced 7.8±3.1% and 19.4±3.9% histamine release, respectively. At 10 min., MCAF/MCP-1 and PF4 induced 2.7±0.9% and 18.8±1.8% histamine release, respectively.

The inhibition of histamine release by a low concentration of MCAF/MCP-1 was very fast, and reached a statistically significant difference in 15 seconds. The peak of inhibition was reached after 3 minutes of preincubation and was sustained thereafter. Once the cells were preincubated with PF4 prior to challenge with MCAF/MCP-1, a statistically significant inhibition of histamine release was reached at about 3 minutes of preincubation. The peak of inhibitory activity by PF4 was attained after 10 minutes preincubation and remained relatively unchanged (a lack of statistically significant difference) up to 30 minutes of preincubation.

The Effect of PF4 on MCAF/MCP-1 and Anti-IgE Induced Histamine Release

Figure 2:
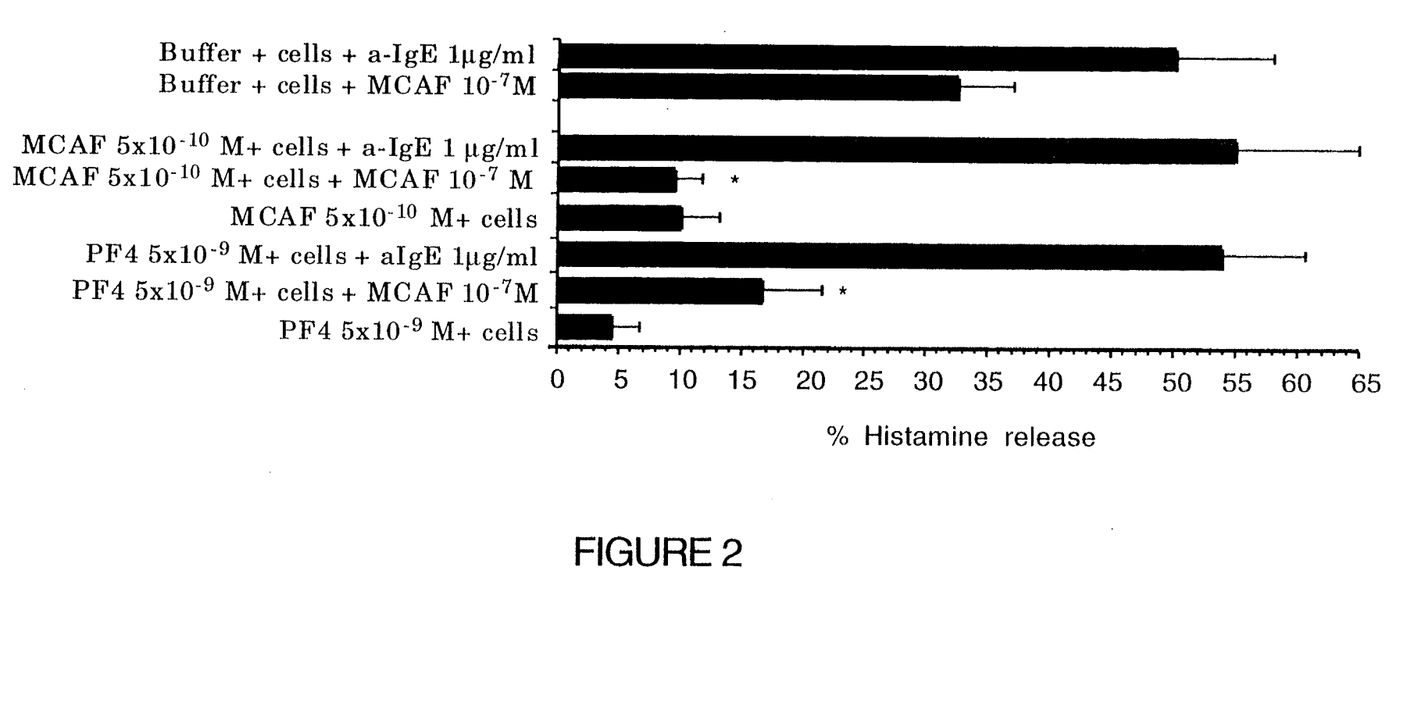
FIG. 2 is a graph showing the effect of MCAF/MCP-1 and PF4 on histamine release induced by anti-IgE and MCAF/MCP-1.

Leukocytes from 13 subjects were tested for inhibition or enhancement of histamine release due to PF4 as well MCAF/MCP-1. The results are presented in FIG. 2, which shows the effect of PF4 on anti-IgE and MCAF/MCP-1 induced histamine release. PF4 inhibited histamine release induced by MCAF/MCP-1, but not by anti-IgE, under these particular in vitro conditions. Leukocytes were preincubated with either buffer alone, MCAF/MCP-1 ($5 \times 10^{-10}$ M) or PF4 ($5 \times 10^{-9}$ M) for 10 minutes at 37° C., and then challenged with anti-IgE (1 µg/ml) or MCAF/MCP-1 ($10^{-7}$ M). Statistical significance is shown versus histamine release induced by MCAF/MCP-1 $10^{-7}$ M; (*) p<0.001. These results confirmed and enlarged upon the data obtained from our dose response and kinetics study.

Inhibition of Histamine Release by PF4 Using Purified Basophils

Figure 3:
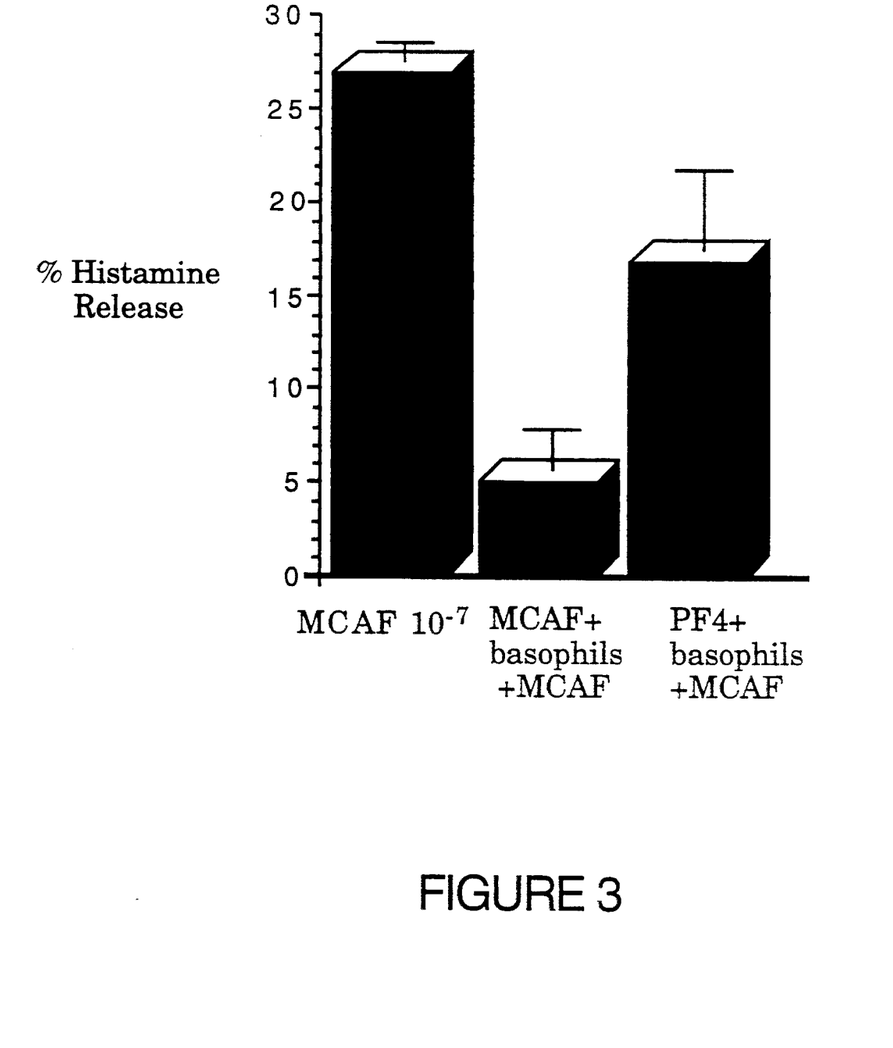
FIG. 3 is a graph showing PF4-dependent inhibition of MCAF/MCP-1-induced histamine release from basophils purified to 80%.

To determine whether the inhibitory effect seen with PF4 is due to a direct interaction with basophils, we preincubated basophils at 80% purity with PF4 for 10 minutes after which MCAF/MCP-1 at a concentration of $10^{-7}$ M was added (FIG. 3). Cells were preincubated with either MCAF/MCP-1 ($5 \times 10^{-10}$ M) or PF4 ($5 \times 9^{-10}$ M) for 10 minutes at 37° C., and then challenged with MCAF/MCP-1 ($10^{-7}$ M) for 40 minutes. Bars represents mean±SEM from four experiments in 50 different donors. A similar pattern of inhibition was seen as with mixed leukocytes in which the percentage of basophils was 0.5–2.0%.

Animal Tests

A widely used animal model of human asthma is the rabbit model described in W. Dorsch, *CRC Handbook on Late Phase Response*, Chap. 35 (1990), which is incorporated herein by reference. In addition, Irvin, *J. Allergy Clin. Immunol.*, 90(3):521–533 (1992), describes a rabbit model for sinusitis, which is incorporated herein by reference.

To test the effectiveness of PF4, PF4 analogs, or fragments thereof, to control asthma, the rabbit asthma model can be used with an aerosol or other challenge with PF4. In order to induce an early- and late-phase asthmatic response, allergic rabbits are anesthetized and restrained on a molded surgical board in the supine position. They are incubated after the method of Zavala et al., *Proc. Soc. Exper. Bios. Med.*, 144:509 (1973), and an esophageal balloon is placed to record transpulmonary pressures and flow. These are used to calculate dynamic compliance ($C_{dyn}$) and total lung resistance ($R_l$) after the method of Davidson et al., *J. Appl. Physiol.*, 21:1094 (1966). A Buxco ® analyzer may be used for automated calculations.

For measurements of allergen sensitivity and demonstration of late responses, the allergen is nebulized with the DeVilhiss ® nebulizer (10,000 PNUs/ml) for 30 s, then for 2 min. separated by 5 min. observation periods. When the transpulmonary pressure has doubled from baseline, the allergen challenge is stopped. For measurements of nonspecific bronchial hyper-responsiveness (NSBHR), histamine is aerosolized for periods of 2 minutes, interposed by 3 minutes of observation, with 0.075–80 mg/ml concentrations of autocoid. Airway sensitivity is estimated by calculating the dose of histamine or allergen in mg/ml which is required to reduce the $C_{dyn}$ by 50% ($PC_{50}C_{dyn}$ histamine, allergen). Airway reactivity is calculated from the slope of the dose response curve after the method of Oreheck et al., *Am. Rev. Respir. Dis.*, 115:937 (1977). The severity and duration of an late-phase asthmatic response (LAR) is qualified by calculating the area (mm$^2$) under the curve described by the late response from 1–6 h for $C_{dyn}$ as previously described in Metzger et al., *Chest*, 88:369 (1985), with the use of a Sigmaplot TM digitizer.

Peripheral blood is obtained throughout challenges from a cannulated ear artery with the use of a Heparin lock, and bronchoalveolar lavage is performed at various times from baseline throughout the challenge, and following challenges, via a small polyethylene catheter inserted into the lung until resistance is felt. Suction is applied through a sterile trap and cells obtained from the bronchoalveolar lavage fluid are cytocentrifuged (Cytospin II, Shandon, P. A. Sweickley), and stained with a Geimsa stain (Dif Quick) or Toludine blue (pH 0.5). For tissue samples, staining for mast cells is carried out after preservation with Carnoy's medium and stained with Toludine blue. Normally, tissue preservation is accomplished with 2.5% glutaraldehyde prior to embedding with JB-4 or Spurr's plastic.

To test PF4, a PF4 analog, or fragment, the rabbit from the above model is challenged with an allergen and treated with a dosage of 100 ng to 1 mg of PF4/inhalation 8 days later. For other modes of administration, the dosage should be about 10 µg to 10 mg/dose. Two weeks later, the same dosage of PF4 is again administered, and the rabbit is then challenged with the same allergen 30 minutes later. The $C_{dyn}$, $R_l$, and $PC_{50}$ are measured before the initial administration of the allergen, and at 24 h, 1 week, and 2 weeks after the second administration of the allergen. An improvement in one or more of the $C_{dyn}$, $R_l$, and $PC_{50}$ of greater than about 20% compared to a control indicates that the protein is effective in vivo. However, any statistically significant clinical improvement can be used as an indication of efficacy.

THERAPY

Administration

The invention is carried out by administering a therapeutically effective amount of PF4, histamine-release-inhibiting PF4 analog, or peptide fragment of PF4 or an analog, to a mammal with an inflammatory, e.g., allergic disease. Administration is by various routes, including, e.g., inhalation of an aerosol (intrabronchial or intranasal), intranasal drops, injection, e.g., intravenous, intraarterial, subcutaneous, intramuscular, or intradermal, or topical application to an affected area of skin or eye. As with any treatment for allergic diseases such as asthma, effective dosage schedules should be tailored to meet the patient's needs, and raised or lowered in proportion to his or her propensity to develop acute episodes, the goal being to maintain the best state of pulmonary function with the minimum amount of treatment.

For inhalation, which is the preferred method of administration for respiratory allergic diseases such as asthma (oral inhalation) and allergic rhinitis (intranasal inhalation), the PF4 or PF4 analog is solubilized and loaded into, e.g., an atomizer or nebulizer, or a pressurized aerosol dispenser, for administration. Such devices are well known in this field. The PF4 or PF4 analog, or peptide fragment, can also be mixed with a pharmaceutically acceptable carrier, e.g., saline. Dosages for a therapeutically effective amount for inhalation range from 100 ng to 1 mg, and preferably 100 ng to 100 $\mu$g, per inhalation. Since PF4 has no known toxic or immunological side effects, a wide range in dosage is appropriate.

For topical administration, e.g., for atopic dermatitis, contact dermatitis, allergic conjunctivitis, urticaria, or any skin lesion that contains mast cells, a therapeutically effective amount of PF4 or PF4 analog or fragment is applied to the site of skin or eye, or is combined with a pharmaceutically acceptable carrier, e.g., a spreadable cream, gel, lotion, or ointment, or a liquid such as saline. For use on the skin, the penetration of the protein into the diseased tissue can be accomplished by a variety of methods known to those of ordinary skill in this field. For example, the protein may be applied directly and mechanically rubbed into the skin. Furthermore, the protein may be incorporated into a transdermal patch that is applied to the diseased skin. Preferably, the penetration resulting from these methods is enhanced with a chemical transdermal delivery agent such as dimethyl sulfoxide (DMSO) or the nonionic surfactant, n-decylmethyl sulfoxide (NDMS) as described in Choi et al., *Pharmaceutical Res.*, 7(11):1099–1106 (1990). Dosages for a therapeutically effective amount for topical application would be in the range of 100 ng to 10 mg per treated surface area or lesion per day.

For systemic administration, an effective amount of PF4 according to the invention is selected to achieve a concentration of 10 ng to 1 mg/ml in the patients blood, and preferably 400 ng to 1 mg/ml. As is known in the medical field, the proper dosage to achieve this blood level of the PF4 protein is best determined by the patient's total skin surface area or weight. The total surface area is based on the patient's weight and height, and is determined by calculation tables. See, e.g., Harrison, *Internal Medicine*. The average person's surface area is about 1.7 m$^2$. Based on this calculation, the dosage should be in the range of 0.1 to 10 mg/m$^2$ of body surface area. If based on only a patient's weight, the dosage should be in the range of about 0.5 to 500 $\mu$g/kg, preferably 20 to 200 $\mu$g/kg. These dosages would be administered on a periodic basis, e.g., daily, weekly, or monthly, depending on clinical symptoms and the patient's response to treatment. Oral dosages would be 5 to 100 times higher than the dosages for injection.

For injection, the PF4 protein is preferably mixed with one or more pharmaceutically acceptable carriers, for example, saline or a physiologic buffer, which are known to those of skill in the art. Of course, in some cases, it may be desirable to incorporate a preservative into this excipient. In addition, the PF4, PF4 analogs, and peptide fragments of the invention can be administered systemically or locally by known sustained-release matrices. Methods for incorporating therapeutic agents, such as the proteins of the invention, into pharmaceutical carriers and sustained-release matrices are well within the skill of the art.

Combinations of PF4 With Other Histamine-Release Inhibiting Agents

PF4 binds to basophils, and MCAF/MCP-1, but not PF4, activates these cells at the concentrations utilized. In allergic diseases such as asthma, or in the late phase reaction that characterizes allergic diseases, PF4 may function as an agonist or antagonist, and its contribution may depend upon the specific concentration, the order in which it is administered, and the responsiveness of the basophils or mast cells in the vicinity. Therefore, combinations of PF4 and other histamine-release inhibiting agents, such as proteins similar to PF4, should also be useful in the methods of the invention. In addition, chimeric proteins including histamine-release inhibiting fragments of PF4 and some other protein may also be used in this method.

OTHER EMBODIMENTS

Other embodiments are within the following claims. It should be understood that the examples and embodiments described herein are for illustrative purposes only, and that various modifications or changes in light thereof will be suggested to persons skilled in the art and are to be included within the scope of the appended claims.

What is claimed is:

1. A method of treating a respiratory allergic disease in a mammal, comprising administering to said mammal a therapeutically effective amount of purified or recombinant platelet factor 4 (PF4).

2. The method of claim 1, wherein said mammal is a human.

3. The method of claim 1, wherein said respiratory allergic disease is asthma.

4. The method of claim 1, wherein said PF4 is administered systemically at a dosage of between 1 to 10 mg/m$^2$ of body surface area of said mammal.

5. The method of claim 1, wherein said PF4 is administered systemically at a dosage of between 0.5 to 500 $\mu$g/kg of body weight of said mammal.

6. The method of claim 1, wherein said PF4 is administered systemically at a dosage of between 20 to 200 $\mu$g/kg of body weight of said mammal.

7. The method of claim 1, wherein said PF4 is administered by inhalation at a dosage of between 10 ng to 1 mg per inhalation.

8. The method of claim 7, wherein said PF4 is administered by inhalation at a dosage of between 100 ng to 100 $\mu$g per inhalation.

9. The method of claim 1, wherein said PF4 is administered by intravenous, intraarterial, intramuscular, subcutaneous, oral, or other systemic administration.

10. A method of treating a respiratory allergic disease in a mammal, comprising administering to said mammal a therapeutically effective amount of a synthetic or recombinant protein having the biological activity of purified or recombinant platelet factor 4 (PF4).

11. The method of claim 10, wherein said mammal is a human.

12. The method of claim 11, wherein said biological activity is the ability to inhibit pro-inflammatory mediator release from basophils or mast cells.

13. The method of claim 12, wherein said pro-inflammatory mediator is histamine.

14. A method of treating bronchoconstriction or bronchial hyper-responsiveness in a mammal, comprising administering to said mammal a therapeutically effective amount of purified or recombinant platelet factor 4 (PF4).

15. The method of claim 14, wherein said PF4 is administered by inhalation at a dosage of between 100 ng to 100 µg per inhalation.

* * * * *